United States Patent [19]

Ralph

[11] Patent Number: 5,836,958
[45] Date of Patent: Nov. 17, 1998

[54] SURGICAL CURETTE HAVING A VARIABLY ANGLED HANDLE

[76] Inventor: James D. Ralph, 71 Manito Ave., Oakland, N.J. 07436

[21] Appl. No.: 741,573

[22] Filed: Oct. 30, 1996

[51] Int. Cl.⁶ ............................. A61B 17/16; A61B 17/24
[52] U.S. Cl. ............................................... 606/160; 606/84
[58] Field of Search ............................. 606/160, 84, 131, 606/159, 161–162

[56] References Cited

U.S. PATENT DOCUMENTS

| | | | |
|---|---|---|---|
| 5,116,346 | 5/1992 | Yeh | 606/131 |
| 5,250,061 | 10/1993 | Michaelson | 606/160 |
| 5,334,212 | 8/1994 | Karell | 606/160 X |
| 5,348,023 | 9/1994 | McLucas | 606/160 X |
| 5,586,989 | 12/1996 | Bray, Jr. | 606/84 X |

Primary Examiner—Michael Buiz
Assistant Examiner—Nancy Connolly Mulcare
Attorney, Agent, or Firm—Joseph P. Errico, Esq.

[57] ABSTRACT

A curette having a variably angled handle includes a curette member which has a disc shaped end. The disc shaped end has a hole through its center and a series of discrete angular graduations on its edge. The disc shaped end is retained via a pin in a recess in the proximal end of a handle. The handle includes an axial bore through which a shaft extends into selective contact with the graduations on the disc shaped end of the curette member. The curette may be angularly positioned relative to the handle if the shaft is selectively disengaged from its contact with the graduations of the disc shaped end of the curette member, but not once the shaft has engaged the graduations. The shaft may be selectively engaged by a variety of different ways, including spring biasing, threading and having a selectively extendable handle.

6 Claims, 2 Drawing Sheets

SURGICAL CURETTE HAVING A VARIABLY ANGLED HANDLE

BACKGROUND OF THE INVENTION

1. Field of the Invention

This invention relates generally to a surgical curette effective for removing tissue from a patient through a small surgical entrance hole, and more particularly to curette having a variably angled handle.

2. Description of the Prior Art

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. The spacers, or intervertebral discs, provide a cushioning for the overall motion of the spine. These discs are generally circular in shape, but have a thickened central portion when measured from edge to edge, therein providing convex upper and lower surfaces. This shape permits the intervertebral disc to conformably fit between axially sequential vertebral bodies, and more particularly to the concave upper and lower surfaces thereof.

Disease, degeneration, and trauma, as well as combinations of the aforementioned, may cause the cartilage to weaken or tear; in severe cases requiring the removal of portions or entireties of disc materials. In severe cases, including instances in which an entire disc has been removed, the immobilization of the local sequence of vertebrae is required to permit ossification into a solid fusion.

The surgical process of removing the intervertebral disc of material generally includes making a small incision to provide access to the anterior portion of the spinal column. Subsequent to access being provided the surgeon must use a small sharp edged spoon-like tool to cut and scoop the defunct tissue from the site. This spoon-like device is referred to as a curette. Referring to FIG. 1, a standard surgical curette is provided in perspective view. This curette 10 of the prior art comprises an elongate body having a gripping surface 12 provided on the end 14 distal from the spoon-like end 16. The edge 18 of the spoon-like end 16 is generally sharpened so as to be able to cut and/or scrape the disc material out, and a concave bowl locus 20 for collecting same.

In instances wherein the entire disc is removed, the sensitivity of the surrounding tissues, the dimensions of the entrance hole and the specific anatomical conformation of the patient often makes accurate and facile manipulation of the curette difficult. This is often so much the case that surgeons are often required to use two hands on the curette handle because of the awkward positions they must contort the tool to reach the disc material. This has a negative impact on the surgical procedure for a variety of reasons, including efficiency and medical accuracy. Most particularly, however, the fixed angle curette is difficult for the surgeon to manage, and therefore has inherent surgical ease problems, which correspondingly effects all other aspects of the surgery.

It is, therefore, an object of the present invention to provide a new and novel curette which ameliorates the difficulties associated with present curettes, and more particularly with the inability to easily manipulate and position the curette in a variety of surgical environments.

SUMMARY OF THE INVENTION

The preceding objects of the invention are achieved by the present invention which is a curette having a variably angling handle, and more specifically to a curette having a handle which may be selectively varied through a variety of angles such that the surgeon may more easily manipulate the spoon-like end of the tool into its needed position. At its most conceptual, the device comprises a handle having a receiving locus at one end thereof, a curette portion having a shaft section and a spoon-like engaging end section, and means for selectively constraining the curette within the receiving locus at a variety of angles relative thereto.

More particularly, with respect to specific embodiments, the handle portion includes an axial bore having a receiving port at one end thereof. A cap element is disposed at the other end of the axial bore, said cap element being coupled to, or integrally formed with, a shaft extending through the bore of the handle. The cap element and shaft are mounted to the handle in such a way that the user may selectively translate the shaft within the bore, but whereby the shaft may also be rigidly fixed at a specific position in the bore. This may be realized by a variety of means, but preferably by spring loading the cap and shaft within the bore or by a mutually engaging threading on the cap and the distal end of the handle.

Inasmuch as the object of this functional component is more specifically to provide for the selective and relative motion of the shaft within the bore from the end of the handle which includes the receiving locus, it may alternatively accomplished by providing a handle portion having a selectively extendable length whereby the end to which the cap element and the shaft are coupled thereto may be selectively extended away from and nearer to the receiving end. This may, for examples, be provided by a pair of threaded and engageable pieces or by a pair of pieces held together by a pin which may be selectively positioned in a set of graduated holes in the central portions of each one of the mutually engageable pair. It shall be understood that the multitude of ways by which this functionality may be achieved are anticipated herein.

The curette portion of the present invention comprises an element having a spoon-like distal end, which may be of the standard type or of an alternative shape. The curette further includes an elongate post extending from the distal end, and ending at a disc-like proximal end. The disc-like proximal end includes a through hole, extending through the planar face of the disc, perpendicular to the face and to the axis of the elongate post of the curette portion. The curette is thereby engaged and retained within the receiving portion of the handle by means of a pin which is perpendicularly fixed within the bore, extending through the hole in the disc, about which the curette may swing.

The circumferential edge of the disc includes a multiplicities of features making angular graduations. These features may be gauges, teeth, or other topological features which permit the physical engagement therewith. The shaft which is disposed in the axial bore of the handle, and which is selectively translatable therein is so disposed so as to engage these topological features of the circumferential surface of the disc-like end of the curette portion. Such engagement thereby locks the curette in angular position relative to the handle. Axial translation of the shaft away from the proximal end of the bore permits the user to selectively disengage the shaft and the angular graduations of the disc, and thereby to freely angulate the curette relative to the handle. Once in the desired position the shaft is selectively advanced back into engagement with the graduations, so as to lock the curette at the chosen angle relative to the handle.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
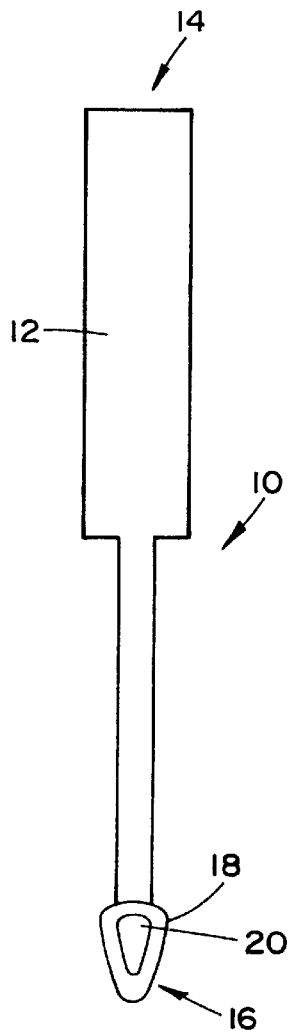
FIG. 1 is a perspective view of an curette of the prior art.
Figure 2:
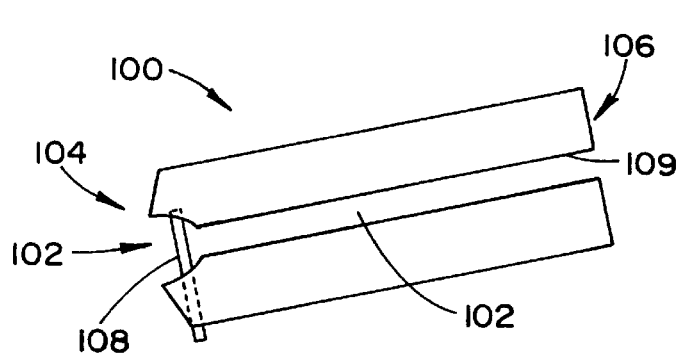
FIG. 2 is a side cross-section view of a handle which is an aspect of the present invention.

Referring now to FIG. 2, a handle of an embodiment of the present invention is shown in a cross-section view. The handle 100 has a generally tubular body which is ideal for manually gripping. The handle 100 further comprises an axial bore 102 extending from a proximal end 104 to the distal end 106. The proximal end of the bore is outwardly tapered to permit the retention of a disc. A pin 108 (for retaining a disc shaped object by positioning through a hole therein, see FIG. 4) is disposed in the proximal end 104 of the bore, aligned perpendicular to the axial bore 102. A receiving locus 107 is thereby defined at one proximal end. The axial bore 102 further includes an annular lip 109 at the distal end 106.

Figure 3:
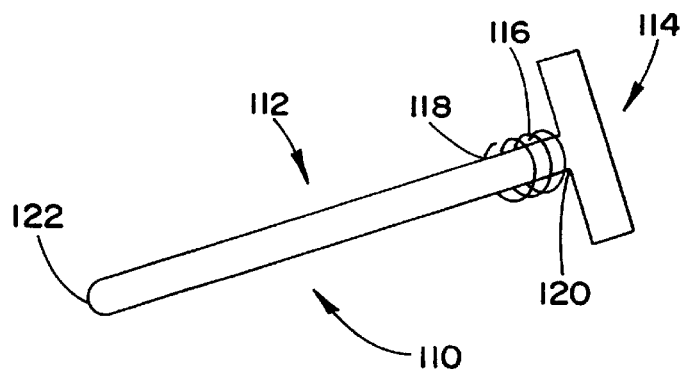
FIG. 3 is a side view of a shaft and cap element of the present invention.

Referring now to FIG. 3, a cap element and shaft 110 is provided. More particularly, this element comprises an integrally formed shaft 112 and a cap 114. The shaft portion 112 is proportioned to fit in the axial bore 102 of the handle 100 so that it may translate freely along the axis of the bore, but be generally constrained from lateral movement in other directions. The cap 114 is generally proportioned to seat against the distal end 106 of the handle. At the interface of the cap 114 and shaft 112 is a spring element 116, one end 118 of which is fixably attached to the shaft 112. The other end 120 is to be biased against the lip 109 on the inner surface of the axial bore 102 of the handle 100. This spring 116 provides a translational bias to the shaft 112 such that it is as far forward in the axial bore 102 as is permitted by the cap's 114 contact with the distal end 106 of the handle 100 permits. In this forwardly biased position, the proximal tip 122 of the shaft 112 is disposed in the receiving locus 107 at the proximal end 104 of the handle. The user, however, may selectively pull the shaft 112 back from the receiving locus 107 by pulling the cap 114 back from engaging the distal end 106 of the handle 100, thereby compressing the spring 116 and counteracting the forward bias thereof.

Figure 4:
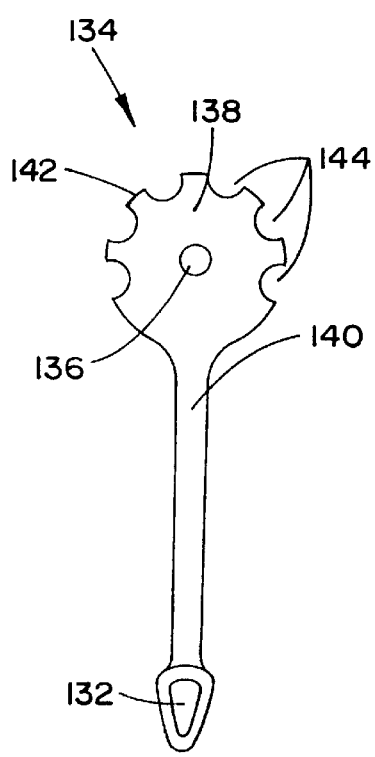
FIG. 4 is a perspective view of the curette portion of the present invention.

Referring now to FIG. 4, the curette element 130 is shown in a side perspective view. The curette 130 is an elongate member having a distal spoon-like end 132, having substantially similar characteristics as other fixed handled curettes. The proximal end 134 of this element 130 is disc shaped. The disc-like proximal end 134 includes a through hole 136, extending through the planar face 138 of the disc, perpendicular to the face and to the axis of the elongate post 140 of the curette portion. The curette 130 is thereby engaged and retained within the receiving portion 107 of the handle 100 by means of the pin 108 therein.

The circumferential edge 142 of the disc 138 includes a multiplicity of angular graduations 144. These graduations 144 are shown herein as serrations, however, it shall be understood that a variety of other topological features, for example teeth, could be utilized in the alternative. These serrations 144 are provided for engagement with the tip 122 of the shaft 112 which extends into the receiving locus 107 via the axial bore 102 of the handle 100.

Figure 5:
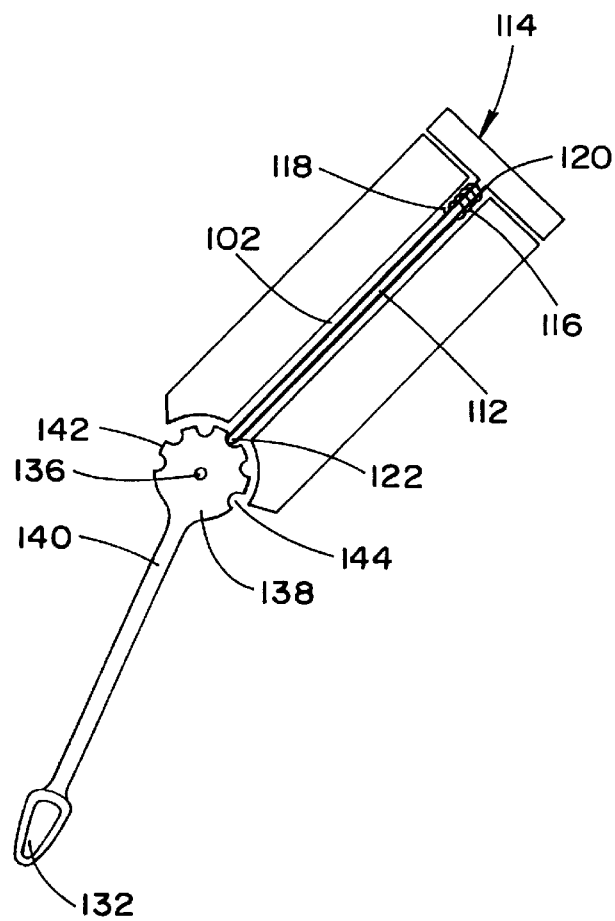
FIG. 5 is a side cross-section view of a variable angulable curette which is an embodiment of the present invention.

Referring now to FIG. 5, the assembled variably angulating handled curette is shown in cross-section. The shaft 112 is disposed within the axial bore 102 of the handle 100 such that it engages the serrations 144 of the disc-like end 134 of the curette element 130. Selective angulation of the curette relative to the handle is achieved by pulling on the cap 114 and disengaging the shaft 112 from the specific serration 144, thereby permitting free rotation of the curette 130 about the pin 108 extending through the hole 136 therein. Reengagement of the tip 122 of the shaft 112 into a given serration 144 locks the curette in position.

While there has been described and illustrated a specific embodiment of a variably angling handled curette, it will be apparent to those skilled in the art that variations and modifications are possible without deviating from the broad spirit and principle of the present invention which shall be limited solely by the scope of the claims appended hereto.

We claim:

1. A surgical curette, comprising:

a handle having a receiving locus formed in a distal end thereof;

a member having a disc shaped proximal end which includes discrete topological features at spaced angular intervals on the surface thereof, and a distal end having a spoon shaped conformation;

first means for retaining the proximal end of said member within said receiving locus, such that said member may rotate within said receiving locus; and second means for selectively engaging at least one of said discrete topological features of said disc shaped proximal end of said member, whereby the member is prevented from further rotation within the receiving locus.

2. A variably angling handled surgical curette, comprising:

a handle having a proximal end, a distal end, and an axial bore extending from said proximal end to said distal end, said axial bore including a receiving locus at the distal end thereof;

a member having a disc shaped proximal end which includes a through hole extending there through and a plurality of discrete topological features at spaced angular intervals on the surface thereof, and a distal end having a spoon shaped conformation;

a pin disposed in the receiving locus of the axial bore, extending through said through hole of the member, thereby retaining the proximal end of said member within said receiving locus, such that said member may angularly rotate relative to the handle while remaining retained within said receiving locus; and a shaft element disposed in said axial bore having a distal end, (said distal end) thereof being selectively engageable with at least one of said discrete topological features of said member, thereby preventing angular rotation of the member relative to the handle; and means for selectively engaging said distal end of said shaft with said at least one of said discrete topological features of said member.

3. The device as set forth in claim 2, wherein said discrete topological features of said disc shaped proximal end of said member comprise serrations.

4. The device as set forth in claim 2, wherein said discrete topological features of said disc shaped proximal end of said member comprise gear teeth.

5. The device as set forth in claim 2, wherein said discrete topological features of said disc shaped proximal end of said member comprise ridges.

6. The device as set forth in claim 2, wherein said means for selectively engaging said shaft with said discrete topological features of said disc shaped proximal end of said member comprises a spring disposed within the axial bore of said handle which biases said shaft into contact with said proximal end of said member, but which may be selectively compressed to disengage the contact of said shaft with said topological features of said disc shaped member, thereby permitting the rotation of said member relative to the handle.

\* \* \* \* \*